United States Patent [19]

Klein

[11] Patent Number: 4,459,105

[45] Date of Patent: Jul. 10, 1984

[54] ORAL SCREEN TEETH POSITIONER

[76] Inventor: Paul E. Klein, 601 First St., Lake Oswego, Oreg. 97034

[21] Appl. No.: 312,696

[22] Filed: Oct. 19, 1981

[51] Int. Cl.³ .............................................. A61C 3/00
[52] U.S. Cl. .......................................... 433/2; 433/6; 433/18
[58] Field of Search ...................... 433/6, 18, 24, 136, 433/137, 140, 229, 2; 128/136

[56] References Cited

U.S. PATENT DOCUMENTS

| | | | |
|---|---|---|---|
| 1,483,694 | 2/1924 | Stukey | 128/136 |
| 1,629,892 | 5/1927 | Storms | 128/136 |
| 2,259,160 | 10/1941 | Glaser | 128/136 |
| 2,627,268 | 2/1953 | Leppich | 128/136 |

*Primary Examiner*—John J. Wilson
*Attorney, Agent, or Firm*—Kolisch, Hartwell & Dickinson

[57] ABSTRACT

An oral-seal-forming pressure-applying orthodontic screen seatable within a person's mouth adjacent labial gum structure in the upper and lower arches. A rim portion defines a working screen area, and supports an elastomeric web portion which spans the screen area. The web portion is stretchable to act against protruding teeth with a tooth-position-correcting force when the screen is seated within a mouth.

1 Claim, 5 Drawing Figures

ORAL SCREEN TEETH POSITIONER

BACKGROUND AND SUMMARY OF THE INVENTION

This invention pertains to orthodontic oral screens, and specifically to such screens which are seatable within a person's mouth adjacent labial gum structure in the upper and lower arches, and which have an elastomeric web portion actable on teeth.

This invention is intended particularly for use on patients who, due to protruding front teeth, have what is termed as an open bite, wherein the upper and lower incisors do not meet when the mouth is closed. This condition, also commonly known as buckteeth, is quite often caused by continued thumb-sucking during the person's youth.

An open bite prevents a person's lips from closing easily during swallowing. In order to compensate for this, such a person will typically use his tongue to seal the open bite during swallowing. Such tongue action causes an undesired orthodontic force which further opens the bite.

In order to prevent use of the tongue in this situation, a conventional oral seal is used which is made of rigid material to conform to the particular tooth structure existing within the patient's mouth. This provides a seal when placed on the central labial surfaces of the upper and lower tooth arches. Such provides a complete seal when the lips are pressed thereagainst during swallowing, obviating any need to use the tongue for that function. Such conventional screens provide an effective seal, but do not provide any tooth-position-correcting force upon the splayed teeth.

It is therefore an object of this invention to provide a screen which applies a tooth-position-correcting force as well as an oral seal.

It is more specifically an object of the invention to provide such a screen which has a relatively rigid outer rim formed to fit the contours of the mouth structure, and a relatively thin elastomeric web portion bounded and supported by such rim portion which stretches over teeth when placed within a patient's mouth.

These and additional objects and advantages of the present invention will be more clearly understood from a consideration of the drawings and the following detailed description of a preferred embodiment.

BRIEF DESCRIPTON OF THE DRAWINGS

DETAILED DESCRIPTION OF THE INVENTION

Figure 3:
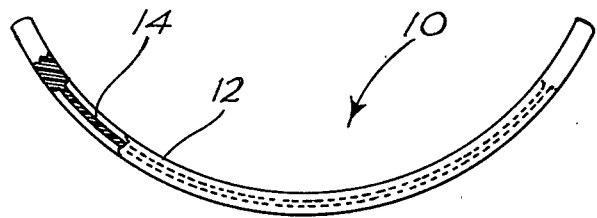
FIG. 3 is a view taken from the top of FIG. 1, with a portion broken away to reveal details of construction.
Figure 2:
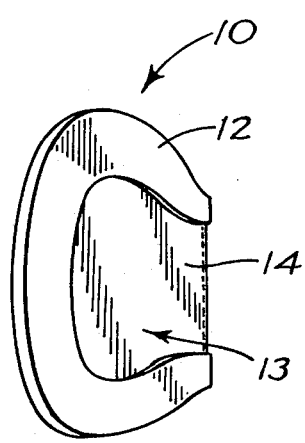
FIG. 2 is a view taken from the left side of FIG. 1.
Figure 1:
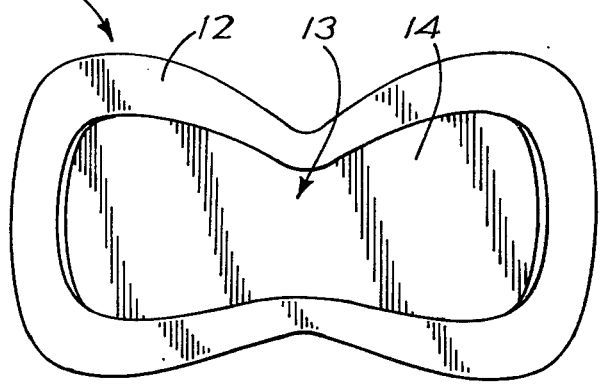
FIG. 1 is a front view of a screen made in conformance with this invention.

Referring initially to FIGS. 1-3, shown generally at 10 is an oral screen constructed as contemplated by this invention. The form and shape of screen 10 is provided by an outer rim 12, also referred to herein both as a rim portion and as a reaction means. Rim 12 is seatable within a person's mouth adjacent labial gum structure in the upper and lower tooth arches and is formed, as shown, to conform to such mouth structure. As can be seen in FIG. 1, rim 12 has a generally horizontally oblong shape with a narrowed or pinched central portion. This is provided in order to accommodate the existence of the centrally located connecting skin tissue attached to the upper and lower tooth arches which are known as the maxillary labial frenom and the mandibular labial frenulum. The exact size of rim 12, perimetrally speaking, is a matter of choice, and preferably will be made available in a range of sizes to fit different mouths.

Figure 5:
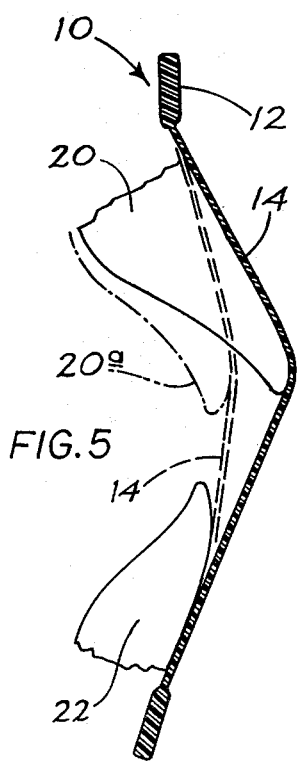
FIG. 5 is an enlarged, fragmentary cross-sectional view of FIG. 4 taken generally along line 5—5 in FIG. 4 to illustrate tooth-position-correcting action performable by the screen of the invention.

As shown in FIG. 5, the rim 12 has a generally rectangular cross-section to provide the rim with sufficient contact surface area to retain its seating against operating forces.

The inner perimeter of rim 12 defines a working screen area 13. This area is spanned by a gas-impermeable elastomeric web 14 which is also referred to herein both as an elastomeric means and as a web portion.

In the illustrated preferred embodiment, rim 12 and web 14 are unitary, and are formed from a mouth-acid-resistant material such as polyureathane resin. Such a material provides both the moderate rigidity required for rim 12 and the resilience and elastic stretchability necessary for thinner web 14. Referring to FIG. 3, this illustrates clearly the unitary nature of web 14 and rim 12. The thickness of web 14 relative to rim 12, as shown in FIG. 3, is not to scale. The thicknesses determine the amount of tooth-correcting force applied by the screen. A thicker web tends to provide a higher force on protruding teeth.

Figure 4:
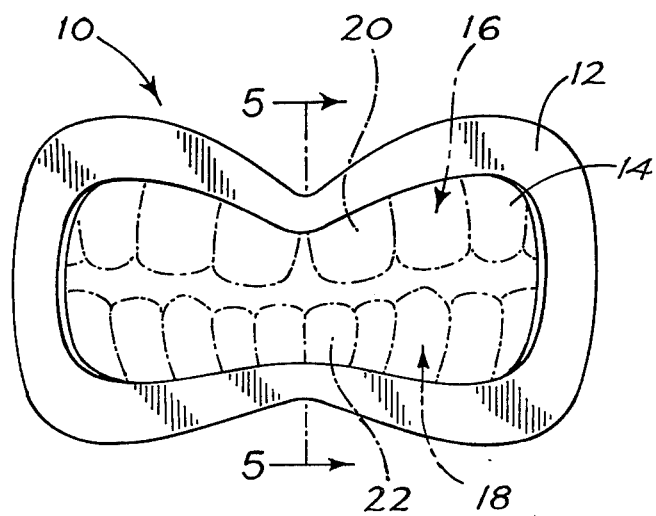
FIG. 4 shows a frontal view of the screen of FIG. 1 in place against upper and lower tooth arches.

FIG. 4 illustrates the positioning of screen 10 adjacent the labial gum structure in an upper tooth arch 16 and in the corresponding opposing lower tooth arch 18. As can be seen, several teeth, including left upper central incisor 20 and left lower central incisor 22 in arches 16, 18, respectively, are covered.

Referring now to FIG. 5, incisor 20 is shown in solid outline protruding outwardly as is typical of an open bite. With screen 10 in place against the upper and lower arches, incisor 20 presses against web 14 causing it to stretch by virtue of rim 12 resisting movement out of its seated position. This stretching causes a generally inwardly directed force on the tooth. After a sufficient period of time, screen 10 causes incisor 20, as well as any other splayed teeth, to return gradually to a more normal position. The resulting, more closed bit is illustrated in dash-dot lines at 20a.

While a unitary structure is disclosed herein, there may be instances where the rim and web portions may be formed preferably as separate pieces, suitably joined thereafter. Also, the web portion may be formed with different selected stiffnesses for different required force applications.

While the invention has been particularly shown and described with reference to the foregoing preferred embodiment, it will be understood by those skilled in the art that other changes in form and detail may be made therein, without departing from the spirit of the invention as defined in the following claims.

It is claimed and desired to secure by Letters Patent:
1. An oral-seal-forming pressure-applying orthodontic screen comprising:
   a rim portion rigidified with a generally rectangular cross-section defining a working screen area, said rim portion being seatable within a person's mouth adjacent labial gum structure in the upper and lower tooth arches, said rectangular cross-section having an elongated length defining a sufficient contact surface area for resistance against operating forces which tend to move said rim portion out of a position seated in the mouth and;

an elastomeric web portion connected to said rim portion and at least partially spanning said screen area, and being stretchable against such resistance provided by said rim portion to act against teeth with a tooth-position-correcting force when said rim portion is seated within a person's mouth.

* * * * *